(12) United States Patent
Gardner

(10) Patent No.: US 9,723,888 B1
(45) Date of Patent: Aug. 8, 2017

(54) NECK AND SPINE SUPPORT SYSTEM WITH ENHANCED USER SAFETY

(71) Applicant: William Chon Gardner, Albuquerque, NM (US)

(72) Inventor: William Chon Gardner, Albuquerque, NM (US)

(*) Notice: Subject to any disclaimer, the term of this patent is extended or adjusted under 35 U.S.C. 154(b) by 174 days.

(21) Appl. No.: 14/658,067

(22) Filed: Mar. 13, 2015

Related U.S. Application Data

(60) Provisional application No. 61/964,707, filed on Jan. 13, 2014.

(51) Int. Cl.
   A42B 3/00       (2006.01)
   A42B 3/04       (2006.01)
   A61F 5/058      (2006.01)
   A61F 5/055      (2006.01)

(52) U.S. Cl.
   CPC .......... *A42B 3/0473* (2013.01); *A42B 3/0466* (2013.01); *A61F 5/055* (2013.01); *A61F 5/05883* (2013.01)

(58) Field of Classification Search
   CPC ..... A42B 3/0466; A42B 3/0473; A61F 5/055; A61F 5/05883
   See application file for complete search history.

(56) References Cited

U.S. PATENT DOCUMENTS

| | | | | |
|---|---|---|---|---|
| 2,820,455 A | * | 1/1958 | Hall | A61F 5/055 128/DIG. 23 |
| 5,195,947 A | * | 3/1993 | Bode | A61F 5/055 602/17 |
| 5,205,803 A | * | 4/1993 | Zemitis | A63B 21/0552 482/121 |
| 5,371,905 A | * | 12/1994 | Keim | A42B 3/0473 2/413 |
| 8,443,468 B2 | * | 5/2013 | Minson | A42B 3/0473 2/468 |
| 2004/0194194 A1 | * | 10/2004 | McNeil | A42B 3/0473 2/421 |
| 2008/0313791 A1 | * | 12/2008 | Nagely | A42B 3/0473 2/425 |
| 2013/0205480 A1 | * | 8/2013 | Nagely | A63B 71/1291 2/425 |

* cited by examiner

*Primary Examiner* — Khaled Annis
(74) *Attorney, Agent, or Firm* — Plager Schack LLP

(57) ABSTRACT

A neck support system to prevent hyperflexion and hyperextension of a spinal cord of a user and enhance user safety connects to both a helmet and shoulder pads worn by the user. The system includes a housing unit having an opening and a first fastening component coupled to a second fastening component disposed on the shoulder pads, a strap retractor mechanism disposed within the housing unit, a strap having a first end coupled to the strap retractor mechanism and a second end having a third fastening component coupled to a fourth fastening component disposed on the helmet. The retractor mechanism enables the extension and retraction of the strap through the housing unit opening to permit freedom of movement of the user's neck. The retractor mechanism locks the strap in a stationary position when a force applied to the strap exceeds a predetermined magnitude of force.

6 Claims, 4 Drawing Sheets

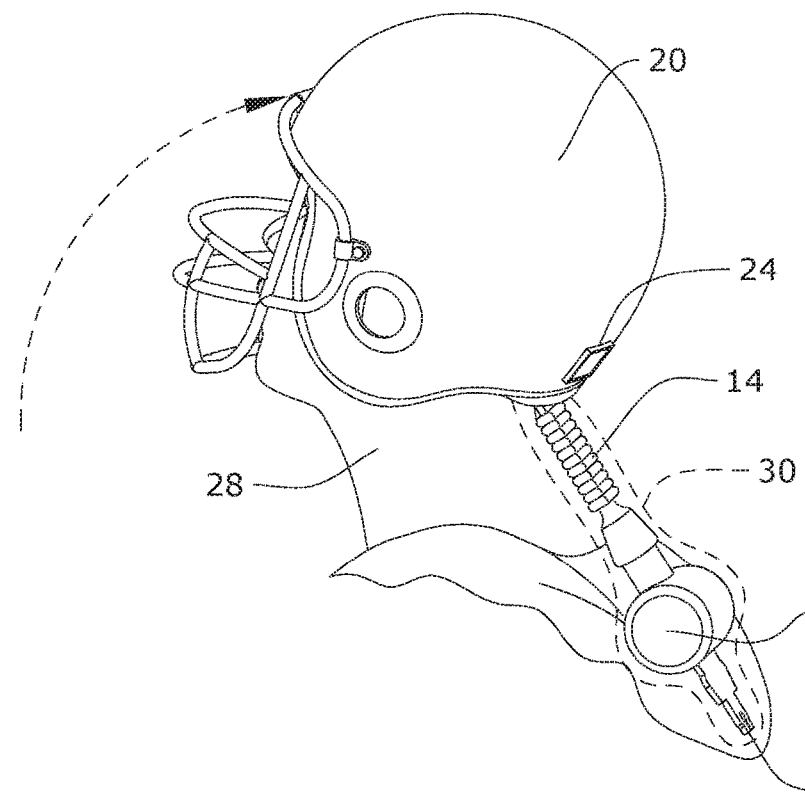
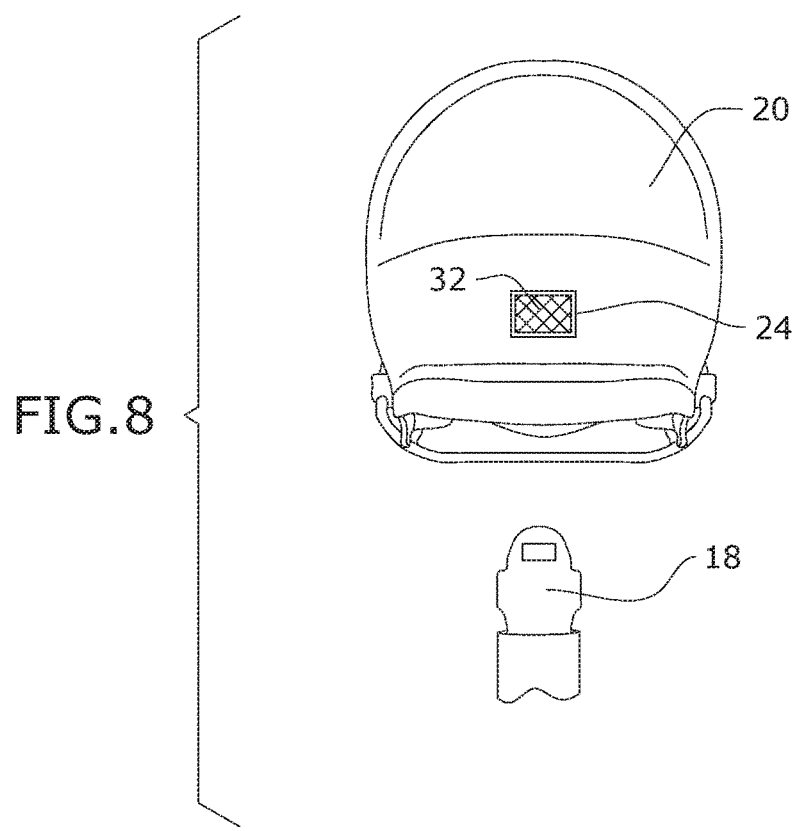

NECK AND SPINE SUPPORT SYSTEM WITH ENHANCED USER SAFETY

RELATED APPLICATION

The application claims priority to provisional patent application U.S. Ser. No. 61/964,707 filed on Jan. 13, 2014, the entire contents of which is herein incorporated by reference.

BACKGROUND

The embodiments herein relate generally to neck and spine support devices for use with individuals who engage in contact sports such as football.

Athletes who engage in contact sports such as football often suffer a variety of serious injuries to the head, neck and shoulder areas. The head and neck areas of football players are particularly vulnerable to injuries. When players collide with each other, a player's neck will often snap with great force, which causes a hyperflexion or hyperextension of the neck and/or spinal chord. In certain circumstances, this force can cause a player to suffer a spinal fracture, paralysis and/or death.

Several devices such as neck rolls or football collars exist to protect the user's neck and spinal chord. However, these devices are limited because they are bulky, uncomfortable and/or impractical for use by players. U.S. Pat. No. 5,371,905 discloses a neck and spine protection device for football players that comprises a fluid dampening hydraulic cylinder assembly connected to the user's helmet and shoulder pads. However, this device is impractical and/or dangerous for use by players. In particular, the components of the hydraulic cylinder assembly add significant weight and bulk to the user, which decreases athletic performance on the field. Moreover, the rigid components of the hydraulic cylinder assembly limit the range of motion of the user's head and neck. In addition, safety concerns arise with the use of the hydraulic cylinder assembly, which can potentially dislodge or disengage upon impact with another individual. Under these circumstances, the sharp ends of the disengaged cylinders can penetrate or stab other players, thereby increasing the risk of injuries to others.

As such, there is a need in the industry for a neck and spine support system with enhanced safety to the user and others, which addresses the limitations of the prior art.

SUMMARY

A neck support system configured to prevent hyperflexion and hyperextension of a spinal cord of a user and enhance user safety is provided. The system is configured to detachably couple to both a helmet and shoulder pads worn by the user. The support system comprises a housing unit comprising an opening and a first fastening component configured to detachably couple with a second fastening component disposed on the shoulder pads, a strap retractor mechanism disposed within the housing unit, a strap comprising a first end coupled to the strap retractor mechanism and a second end comprising a third fastening component configured to detachably couple with a fourth fastening component disposed on the helmet, wherein the retractor mechanism is configured to enable the extension and retraction of the strap through the housing unit opening to permit freedom of movement of the user's neck, wherein the retractor mechanism is configured to lock the strap in a stationary position when a force applied to the strap exceeds a predetermined magnitude of force, thereby preventing the hyperflexion and hyperextension of the user's spinal chord.

BRIEF DESCRIPTION OF THE FIGURES

The detailed description of some embodiments of the invention will be made below with reference to the accompanying figures, wherein the figures disclose one or more embodiments of the present invention.

FIG. 7 depicts a side perspective view of certain embodiments of the neck support system shown in use; and FIG. 8 depicts a rear view of a visual indicator of the helmet used with the neck support system.

DETAILED DESCRIPTION OF CERTAIN EMBODIMENTS

Figure 1:
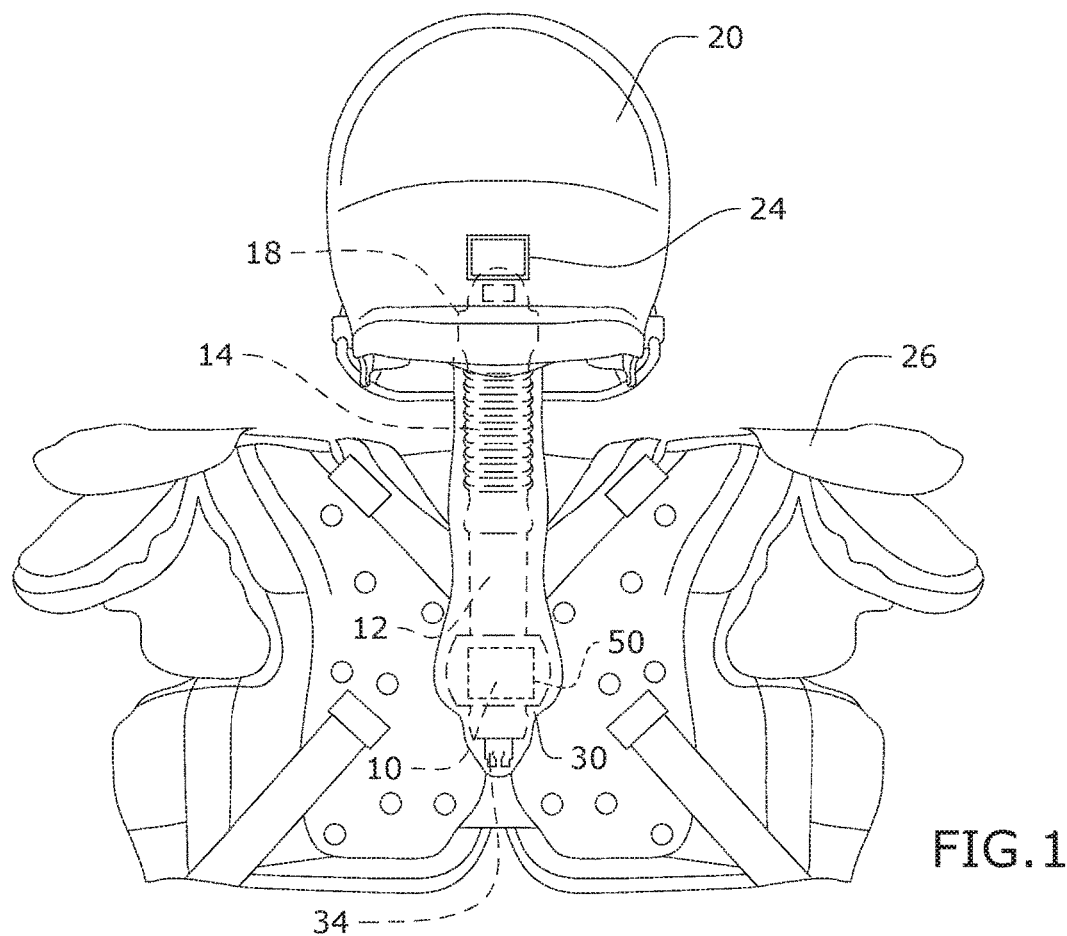
FIG. 1 depicts a rear view of certain embodiments of the neck support system shown in use.
Figure 2:
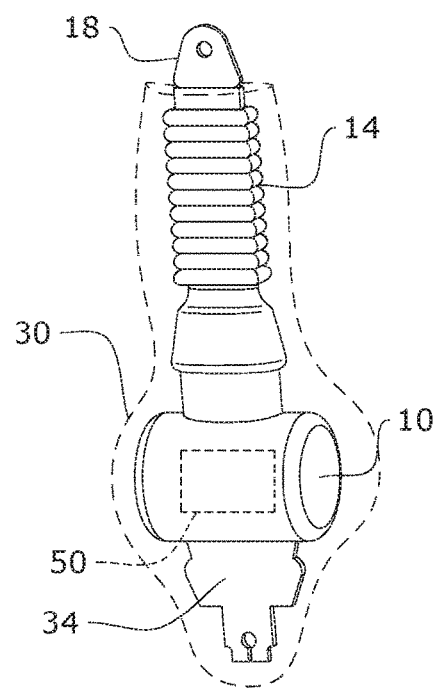
FIG. 2 depicts a perspective view of certain embodiments of the neck support system.

As depicted in FIGS. 1-2, the neck support system is configured to engage and disengage with both helmet 20 and shoulder pads 26. Helmet 20 and shoulder pads 26 may be of any type known in the field. The neck support system comprises housing unit 10, strap 12, sleeve 14 and padding 30. Housing unit 10 stores strap retractor mechanism 50. An opening in housing unit 10 receives a first end of strap 12, which is operably connected to strap retractor mechanism 50. It shall be appreciated that housing unit 10 may comprise any alternative shapes and/or dimensions.

Strap retractor mechanism 50 permits an adjustment of strap 12 to extend out of the opening of housing unit 10 and retract back into housing unit 10 to the stored position. It shall be appreciated that strap retractor mechanism 50 may contain components such as a spool and device to provide sufficient tension on strap 12 to permit the strap to retract back into housing unit 10 after the strap is pulled out of housing unit 10. Housing unit 10 comprises male clip 34, which is configured to detachably couple with a corresponding female clip receiver (not shown) disposed on shoulder pads 26.

Figure 3:
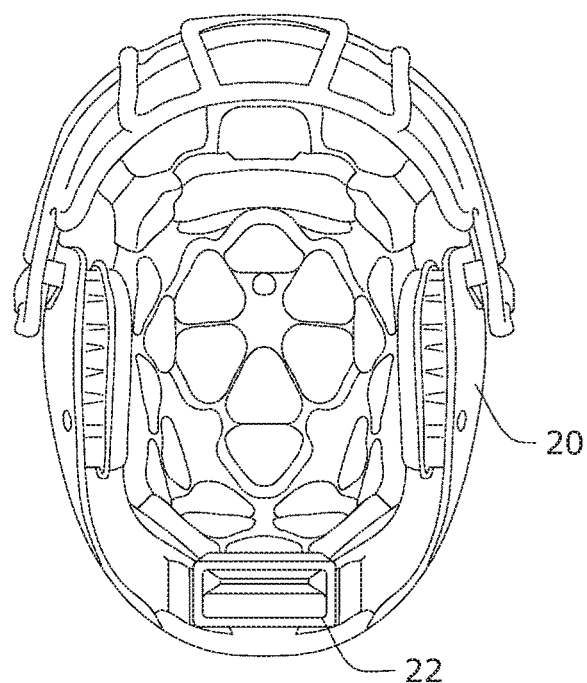
FIG. 3 depicts a bottom view of a helmet used with the neck support system.
Figure 4:
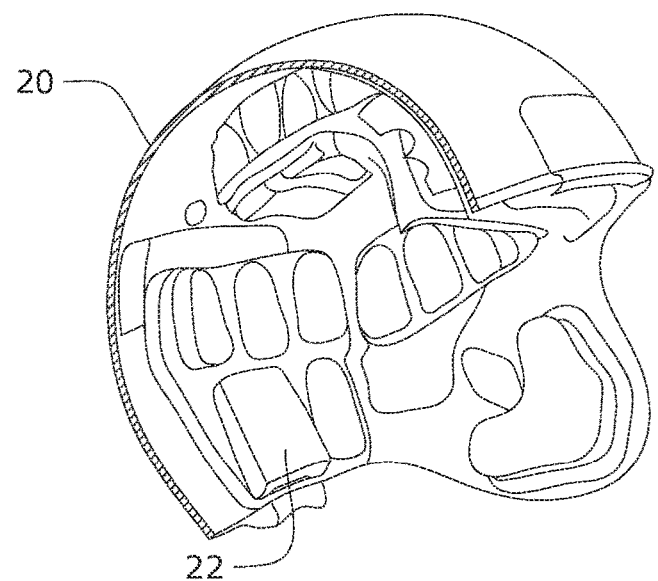
FIG. 4 depicts a cutaway view of the helmet used with the neck support system.

Strap 12 is made from a fabric material such as polyester and may have variable dimensions to accommodate users of different size, athletic ability and age. Typically, strap 12 may have a length that is approximately 4-20 inches. The second end of strap 12 comprises male clip 18, which is configured to detachably couple with female clip receiver 22 of helmet 20. As depicted in FIGS. 3-4, female clip receiver 22 is affixed to the interior of helmet 20. This location permits male clip 18 of strap 12 to easily engage and disengage with female clip receiver 22 when helmet 20 is worn by the user. It shall be appreciated that alternative fastening and anchoring components may be used to secure the neck support system to helmet 20 and shoulder pads 26 such as hooks and loops, snap-fit components, or the like.

Sleeve 14 is disposed around strap 12 and is made from a rubberized and weatherproof material. The first end of sleeve 14 is secured to a lip (not shown) or alternative fastening component on male clip 18. The second end of sleeve 14 is secured to the opening in housing unit 10 and/or portion of strap 12. Sleeve 14 is an elastic member that acts as a shock absorber and provides additional support to the neck support system. The second end of sleeve 14 comprises sufficient dimensions to prevent strap 12 from fully retracting into housing unit 10. Padding 30 is disposed around housing unit 10, strap 12 and sleeve 14, and provides additional support, cushion and durability to the neck support system. Padding 30 may be made from any materials known in the field including, but not limited to, plastic, carbon fiber, shock-absorbing foam, or the like.

Figure 5:
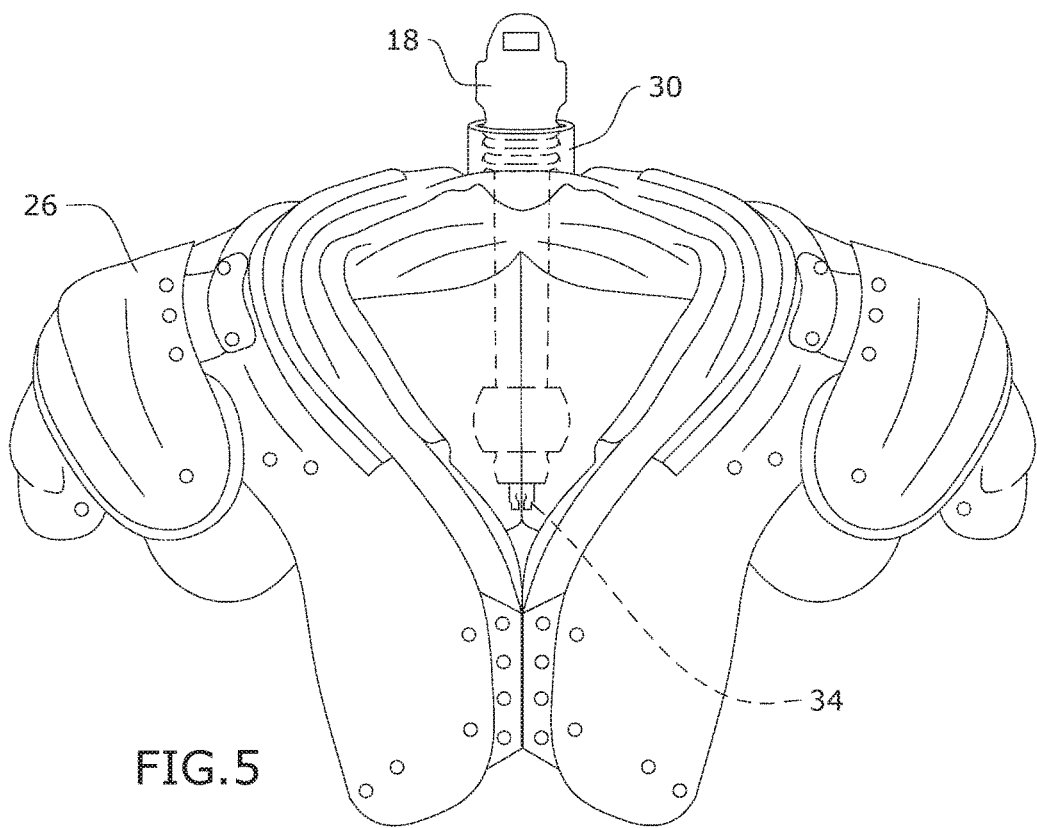
FIG. 5 depicts a front view of certain embodiments of the neck support system.
Figure 6:
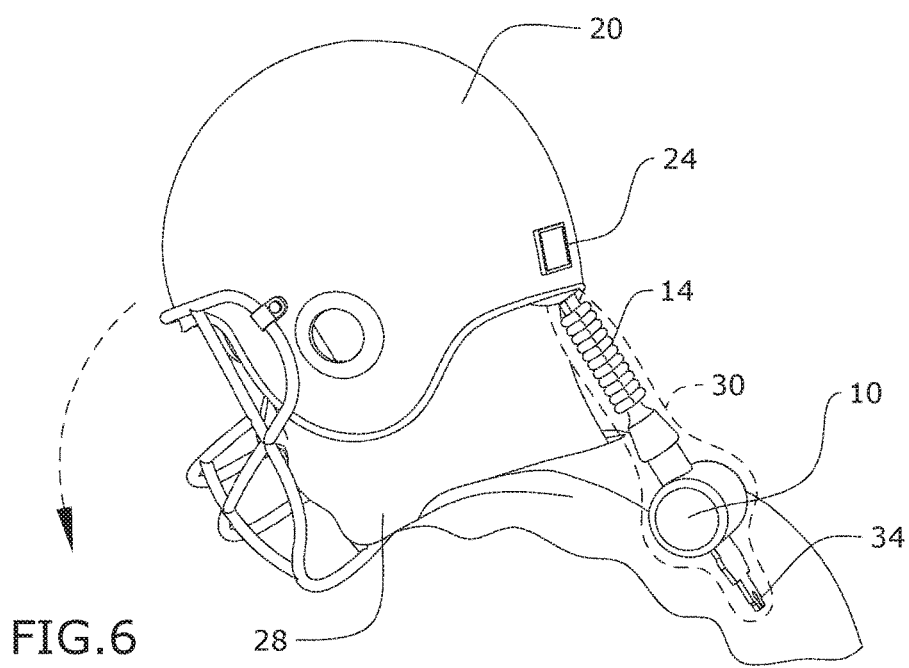
FIG. 6 depicts a side perspective view of certain embodiments of the neck support system shown in use.

FIG. 5 depicts the position and orientation of the neck support system relative to shoulder pads 26 when in use. In operation, the neck support system is secured to helmet 20 and shoulder pads 26 as shown in FIG. 1. The strap retractor mechanism permits strap 12 to extend or retract relative to housing unit 10 when the force applied to strap 12 is below a predetermined magnitude of allowable force. This enables the user to freely move his/her head when the neck support system is secured to helmet 20 and shoulder pads 26. If the force applied to strap 12 exceeds the predetermined magnitude of allowable force, the strap retractor mechanism locks strap 12 in a stationary position until the applied force falls below the predetermined magnitude of allowable force. FIG. 6 depicts an abrupt forward force applied to user 28. If the forward force exceeds the predetermined magnitude of allowable force, strap 12 will lock and prevent the user's neck from snapping forward. FIG. 7 depicts an abrupt backward force applied to user 28. Under this circumstance, the second end of sleeve 14 prevents strap 12 from fully retracting into housing unit 10. This provides sufficient support to prevent the user's neck from snapping backward. As a result, the neck support system effectively prevents hyperflexions and hyperextensions of the user's neck and spinal cord.

As depicted in FIG. 8, an alternative embodiment of helmet 20 comprises visual indicator 24. Visual indicator 24 enables a user to determine if male clip 18 is engaged with helmet 20. If male clip 18 is disengaged with helmet 20, visual indicator 24 displays a first image 32. If male clip 18 is engaged with helmet 20, visual indicator 24 displays a second image. It shall be appreciated that the first image and second image are preferably different colors and/or patterns to clearly indicate whether the neck support apparatus is properly engaged to ensure the safety of user 28.

It shall be appreciated that the components of the neck support system described in several embodiments herein may comprise any alternative known materials in the field and be of any color, size and/or dimensions. It shall be appreciated that the components of the neck support system described herein may be manufactured and assembled using any known techniques in the field. While the embodiments of the invention describe the neck support system for use in football, it shall be appreciated that the system may be used in any alternative sports and/or activities such as hockey, lacrosse, or the like.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A neck support system designed to prevent hyperflexion and hyperextension of a spinal cord of a user and enhance user safety, the system designed to detachably couple to both a helmet and shoulder pads worn by the user, the support system comprising:
   a housing unit comprising an opening and a first fastening component designed to detachably couple with a second fastening component disposed on the shoulder pads;
   a strap retractor mechanism disposed within the housing unit;
   a strap comprising a first end coupled to the strap retractor mechanism and a second end comprising a third fastening component designed to detachably couple with a fourth fastening component disposed on the helmet; and
   a visual indicator coupled to the helmet, the visual indicator designed to display a first image when the third fastening component disengages with the fourth fastening component and a second image when the third fastening component engages with the fourth fastening component;
   wherein the strap retractor mechanism is designed to enable the extension and retraction of the strap through the housing unit opening to permit freedom of movement of the user's neck, wherein the strap retractor mechanism is designed to lock the strap in a stationary position when a force applied to the strap exceeds a predetermined magnitude of force for preventing the hyperflexion and hyperextension of the user's spinal cord.

2. The neck support system of claim 1, further comprising a sleeve disposed around the strap, the sleeve comprising a first end coupled to the third fastening component of the strap and a second end coupled to a portion of the strap.

3. The neck support system of claim 2, further comprising a padding layer disposed around the housing unit, the strap and the sleeve.

4. The neck support system of claim 3, wherein the first fastening component comprises a male member and the second fastening component comprises a female member, wherein the first fastening component is configured to engage with the second fastening component.

5. The neck support system of claim 4, wherein the third fastening component comprises a male member and the fourth fastening component comprises a female member, wherein the third fastening component is configured to engage with the fourth fastening component.

6. A neck support system designed to prevent hyperflexion and hyperextension of a spinal cord of a user and enhance user safety, the system designed to detachably couple to both a helmet and shoulder pads worn by the user, the support system comprising:
   a housing unit comprising an opening and a first fastening component designed to detachably couple with a second fastening component disposed on the shoulder pads;
   a strap retractor mechanism disposed within the housing unit;
   a strap comprising a first end coupled to the strap retractor mechanism and a second end comprising a third fastening component designed to detachably couple with a fourth fastening component disposed on the helmet;
   a sleeve disposed around the strap, the sleeve comprising a first end coupled to the third fastening component of the strap and a second end coupled to a portion of the strap;
   a padding layer disposed around the housing unit, the strap and the sleeve; and a visual indicator coupled to the helmet, the visual indicator designed to display a first image when the third fastening component disengages with the fourth fastening component and a second image when the third fastening component engages with the fourth fastening component;

wherein the strap retractor mechanism is designed to enable the extension and retraction of the strap through the housing unit opening to permit freedom of movement of the user's neck, wherein the strap retractor mechanism is designed to lock the strap in a stationary position when a force applied to the strap exceeds a predetermined magnitude of force for preventing the hyperflexion and hyperextension of the user's spinal cord.

* * * * *